US00PP32507P2

(12) United States Plant Patent
Lee

(10) Patent No.: US PP32,507 P2
(45) Date of Patent: Nov. 24, 2020

(54) ***RHODODENDRON* PLANT NAMED 'ROBLEZF'**

(50) Latin Name: *Rhododendron hybrida*
Varietal Denomination: ROBLEZF

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 16/602,846

(22) Filed: Dec. 10, 2019

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238
CPC ..... A01H 6/364
See application file for complete search history.

*Primary Examiner* — Anne Marie Grunberg
(74) *Attorney, Agent, or Firm* — Cassandra Bright

(57) ABSTRACT

A new and distinct *Rhododendron* cultivar named 'ROBLEZF' is disclosed, characterized by white flowers, and stable variegated leaves. Plants are compact and rebloom during Spring, Summer and Fall. The new cultivar is a *Rhododendron*, suitable for ornamental garden purposes.

1 Drawing Sheet

Latin name of the genus and species: *Rhododendron hybrida.*

Variety denomination: 'ROBLEZF'.

BACKGROUND OF THE INVENTION

The new cultivar is a product of a naturally occurring branch mutation of *Rhododendron* 'Robler', U.S. Plant Pat. No. 18,416, also known as 'Mootum'. This new variety, hereinafter referred to as 'ROBLEZF', was discovered in the Summer of 2012 at a nursery in Independence, La.

After identifying the new variety as a potentially interesting selection, the inventor first organized propagation of 'ROBLEZF' by semi-softwood cuttings in 2012 at a nursery in Independence, La. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'ROBLEZF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROBLEZF' These characteristics in combination distinguish 'ROBLEZF' as a new and distinct *Rhododendron* cultivar:

1. Stable variegated leaves.
2. White flowers.
3. Spring, Summer, and Fall blooming.
4. Compact plant habit.
5. Good specimen plant.
6. Excellent performance in planters.
7. Very good foundation plant.

8. Does well as an understory plant in a woodland garden.
9. Hardy to Zone 7.
10. Attracts butterflies.

COMPARISON TO PARENT VARIETY

'ROBLEZF' is similar in most horticultural characteristics to the parent, however, plants of the new cultivar 'ROBLEZF' however differ in the following:

1. The new variety has variegated foliage, the parent has solid green foliage.

COMMERCIAL COMPARISON

'ROBLEZF' can be compared to the commercial variety *Rhododendron* hybrid 'Roblem', U.S. Plant Pat. No. 15,043. Plants of the new cultivar 'ROBLEZF' are similar to plants of 'Roblem' in most horticultural characteristics, however, plants of the new cultivar 'ROBLEZF' differ in the following:

1. Flowers of 'ROBLEZF' are solid white, flowers of 'ROBLEM' have pink speckles.
2. Foliage of 'ROBLEZF' is variegated, foliage of 'Roblem' is solid light green.

'ROBLEZF' can be compared to the commercial variety *Rhododendron* hybrid 'Silver Sword', unpatented. Plants of the new cultivar 'ROBLEZF' are similar to plants of 'Silver Sword' in most horticultural characteristics, however, plants of the new cultivar 'ROBLEZF' differ in the following:

1. Flowers of 'ROBLEZF' are white, flowers of 'Silver Sword' are pink.
2. Foliage of 'ROBLEZF' is smaller.
3. Plants of 'ROBLEZF' rebloom, plants of 'Silver Sword' do not have recurring blooming.

BRIEF DESCRIPTION OF THE PHOTOGRAPH

The accompanying photograph illustrates in full color a typical flowering plant of 'ROBLEZF' in a 2 gallon pot at approximately 2 years of age. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ROBLEZF' plants grown outdoors in Loxley, Ala. Plants are approximately 2 years old, in a 3 gallon nursery container. Measurements and numerical values represent averages of typical plant types.

Botanical classification: *Rhododendron hybrida* 'ROBLEZF'.

PROPAGATION

Typically by semi-hardwood cuttings in Spring and Summer.

Root description: Fine, fibrous young roots, well branched. Colored near RHS Brown 200C and 200D.

PLANT

Growth habit: Compact, globular shrub.

Height: Approximately 32 cm to top of foliar and flowering plane.

Plant spread: Approximately 40 cm.

Branching characteristics: Moderately branched, approximately 4 to 5 primary branches from the center of the plant. Branches occur at approximately 45 degree angles from center. Main branches produce 2 to 3 lateral branches.

Primary branches:

Length of primary branches: Average 12 to 16 cm.

Diameter of primary branches: Average range 4 to 7 mm.

Primary branch strength: Strong, slightly brittle.

Primary branch color: Near RHS Brown 200D. With age scales colored near Brown N200C. New growth near Yellow-Green 145A.

Primary branch texture: Young growth hirsute, hairs, approximately 0.15 cm long, colored near RHS Greyed-Orange 175A. Older growth scaly.

Lateral branches:

Number of lateral branches: Approximately 2 to 3 per primary branch.

Length of lateral branches: Average 6 to 14 cm.

Diameter of lateral branches: Average 4 mm.

Lateral branch strength: Very strong, flexible.

Lateral branch color: Near RHS Greyed-Orange 175A, flushed Grey-Brown 199D.

Lateral branch texture: Hirsute.

Internode length: Range between 5 to 20 mm.

Age of plant described: Approximately 2 years.

FOLIAGE

Leaf:

*Type*.—Simple.

*Arrangement*.—Alternate.

*Average length*.—Approximately 3.3 cm.

*Average width*.—Approximately 1.8 cm.

*Shape of blade*.—Obovate.

*Apex*.—Acute or broad acuminate.

*Base*.—Broad attenuate.

*Attachment*.—Petiolate.

*Margin*.—Entire.

*Texture of top surface*.—Pubescent. Hairs appressed.

*Texture of bottom surface*.—Pubescent. More hairs present along main vein and margin.

*Foliage scent*.—None.

*Color*.—Young foliage upper side: Center color near RHS Green 137A and 137B, present individually. Strong variegation near RHS Yellow 10A and Green-yellow 1C, colors present individually. Young foliage under side: Center color near RHS Green 138A. Strong variegation near Yellow-Green 151D. Mature foliage upper side: Center color near RHS Green 137B and 137C, present individually. Strong variegation near Yellow 10B. Mature foliage under side: Center color near RHS Green 138A. Strong variegation near Yellow-Green 151D.

Venation:

*Type*.—Pinnate. Venation color upper side: Near RHS Yellow-Green 151C. Venation color under side: Near RHS Yellow-Green 151D.

Petiole:

*Length*.—About 2 mm.

*Diameter*.—About 2 mm.

*Color*.—Upper Surface: Near RHS Yellow-Green 151C. Lower Surface: Near RHS Yellow-Green 151D.

FLOWER

Bloom period: Plants flower in the Spring, then begin intermittent flowering cycles in late Spring/Summer through Fall.

Flower:

*Arrangement*.—Axillary clusters of perfect, double, funnel shaped individual flowers. Typically 4 flowers per cluster.

Inflorescence:

*Height*.—Average 6.0 cm.

*Diameter*.—Average 9.0 cm.

Peduncle: None, inflorescence begins on stem.

Flowers:

*Length*.—Average 3.8 cm.

*Diameter*.—Average 5.2 cm.

*Facing direction*.—Outwardly and upwardly facing.

*Persistent or self-cleaning*.—Petals self-cleaning.

*Fragrance*.—Light, fresh scent.

Tube:

*Tube length*.—Approximately 1.1 cm.

*Tube width a widest point*.—Approximately 9 mm.

*Tube width and narrowest point*.—Approximately 4 mm.

Petals:

*Unfused petal segments*.—Length: Approximately 2.2 cm. Width: Approximately 1.5 cm.

*Apex*.—Retuse.

*Shape of petal*.—Unfused portion, obovate.

*Petal margin*.—Entire. Slightly ruffled aspect along margin.

*Petal arrangement*.—Approximately ⅓ fused from base.

*Petal number*.—Average 12.

*Petal texture*.—Smooth.

*Color*.—Upper surface at first opening: Near RHS White 155D. Under surface at first opening: Near RHS White 155D. Inner surface at maturity: Near RHS White 155D. Outer surface at maturity: Near RHS White 155D. Upper surface at fading: Near RHS White 155D. Under surface at fading: Near RHS White 155D.

Bud:

*Shape*.—Elliptic.

*Length*.—3.2 cm.

*Diameter*.—1.0 cm.

*Color*.—Near RHS White 155D, lightly flushed Green-White 155A.

Calyx/sepals:

*Quantity per flower*.—5 sepals.

*Shape*.—Rounded deltate.

*Length*.—2 to 5 mm.

*Width*.—3 mm.

*Apex*.—Acute.

*Base*.—Fused.

*Margin*.—Entire.

*Texture*.—Highly pubescent.

*Color*.—Inner Surface: Near RHS Yellow-Green 145C. Outer Surface: Near RHS Yellow-Green 145C, margin White 155D.

REPRODUCTIVE ORGANS

Stamens:

*Number*.—Most commonly 0, occasionally 1.

*Length*.—Almost entirely fused to inner petal. Unfused section about 2 mm.

*Width*.—1 mm.

*Color*.—Near RHS White 155D.

*Anthers*.—Length: Approximately 2 mm. Color: Near RHS Yellow-White 158A. Pollen: Not observed to date.

Pistil:

*Number*.—1.

*Length*.—3.9 cm.

*Style*.—Length: 3.0 cm. Color: Near RHS Green-White 157D.

*Stigma*.—Globular, colored near RHS Yellow-Green 145D.

*Ovary*.—Sericeous texture. Approximately 3 mm in diameter, 4 mm long. Colored near RHS Yellow-Green 145A. Hairs colored near RHS White 155D.

OTHER CHARACTERISTICS

Disease and pest resistance: Not observed to be susceptible nor resistant to normal diseases and pests of *Rhododendron*.

Temperature tolerance: USDA Zone 6.

Fruit/seed production: Not observed to date.

What is claimed is:

1. A new and distinct cultivar of *Rhododendron* plant named 'ROBLEZF' as herein illustrated and described.

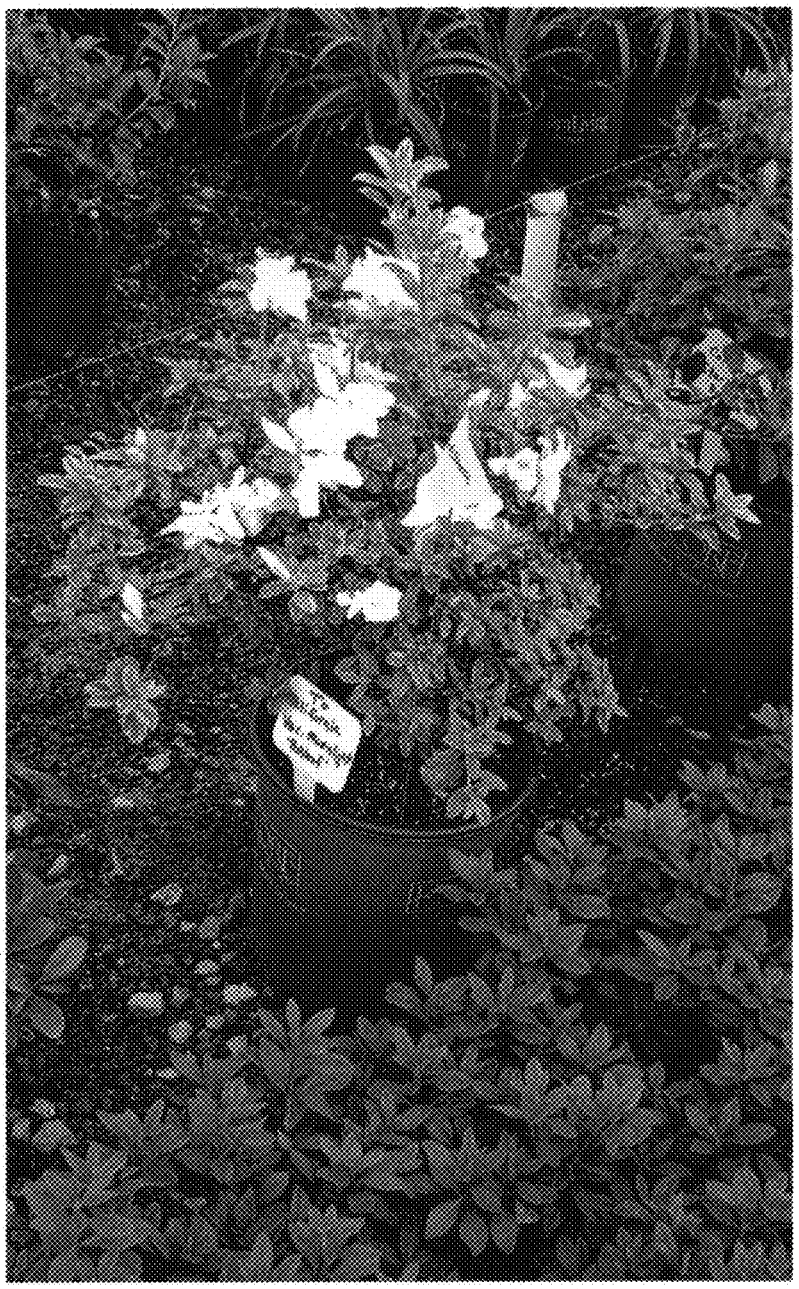

* * * * *